(12) United States Patent
Gotnam

(10) Patent No.: US 10,218,750 B2
(45) Date of Patent: Feb. 26, 2019

(54) COMMUNICATION OF IMAGING SYSTEM INFORMATION

(75) Inventor: Shlomo Gotnam, Haifa (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1229 days.

(21) Appl. No.: 13/881,162

(22) PCT Filed: Oct. 13, 2011

(86) PCT No.: PCT/IB2011/054523
§ 371 (c)(1),
(2), (4) Date: Apr. 24, 2013

(87) PCT Pub. No.: WO2012/056351
PCT Pub. Date: May 3, 2012

(65) Prior Publication Data
US 2013/0219018 A1  Aug. 22, 2013

Related U.S. Application Data

(60) Provisional application No. 61/407,042, filed on Oct. 27, 2010.

(51) Int. Cl.
*G06F 15/16* (2006.01)
*H04L 29/06* (2006.01)
*A61B 6/00* (2006.01)
*G06F 19/00* (2018.01)

(52) U.S. Cl.
CPC ............... *H04L 65/40* (2013.01); *A61B 6/54* (2013.01); *A61B 6/563* (2013.01); *G06F 19/328* (2013.01); *G06F 19/3418* (2013.01)

(58) Field of Classification Search
CPC ...................................................... H04L 65/40
USPC ................................................. 709/217, 218
See application file for complete search history.

(56) References Cited

U.S. PATENT DOCUMENTS

| | | | |
|---|---|---|---|
| 5,715,823 A | 2/1998 | Wood et al. | |
| 6,272,469 B1 | 8/2001 | Koritzinsky et al. | |
| 2002/0143857 A1 | 10/2002 | Bidarahalli et al. | |
| 2003/0114753 A1 | 6/2003 | Sharma et al. | |
| 2003/0126307 A1 | 7/2003 | Lindner et al. | |
| 2004/0139190 A1* | 7/2004 | Kreger et al. | 709/224 |
| 2006/0173713 A1 | 8/2006 | Petro et al. | |

(Continued)

FOREIGN PATENT DOCUMENTS

EP   0890919 A1   1/1999

*Primary Examiner* — Adnan M Mirza

(57) ABSTRACT

A method for exposing imaging system events in connection with an event driven imaging system includes detecting an imaging system event occurred, wherein the imaging system event corresponds to an imaging examination being performed, generating a signal indicative of the detected imaging system event, and transmitting the signal over a computer network for reception by at least one device communicating over the network. A method for exposing imaging system protocol information in connection with an imaging system includes detecting at least one of utilizing of medication to, an addition of or a deletion of an imaging system protocol from the imaging system, generating a signal indicative of the protocol, and transmitting the signal over a computer network for reception by at least one device communicating over the network.

23 Claims, 3 Drawing Sheets

(56) References Cited

U.S. PATENT DOCUMENTS

2007/0109294 A1* 5/2007 Gotman et al. ............... 345/418
2007/0211756 A1   9/2007 Glaser-Seidnitzer et al.
2008/0119717 A1   5/2008 Profio et al.

* cited by examiner

COMMUNICATION OF IMAGING SYSTEM INFORMATION

CROSS REFERENCE TO RELATED APPLICATIONS

This application is a national filing of PCT application Serial No. PCT/IB2011/054523, filed Oct. 13, 2011, published as WO 2012/056351 A1 on May 3, 2012, which claims the benefit of U.S. provisional application Ser. No. 61/407,042 filed Oct. 27, 2010, which is incorporated herein by reference.

The following generally relates to imaging systems and is described with application to computed tomography (CT) and particularly with conveying imaging system information between the imaging system and one or more other systems. The following is also amenable to other imaging modalities such as positron emission tomography (PET), single photon emission tomography (SPECT), magnetic resonance imaging (MRI), ultrasound (US) imaging, digital radiography, and/or other imaging modalities.

A computer tomography (CT) scanner includes an x-ray tube that emits radiation. A source collimator is disposed between the x-ray tube and an examination region and collimates the emitted radiation to produce a fan or cone shaped x-ray beam. The collimated beam traverses the examination region and an object or subject therein (which attenuates the beam as a function of the radiodensity of the object or subject) and illuminates a detector array disposed across the examination region from the x-ray tube. The detector produces projection data indicative of the detected radiation, and the projection data has been reconstructed to generate volumetric image data indicative of the object or subject.

With today's CT scanners, the volumetric image data can be transmitted, electronically, over a secured network for the transmission of patient information, by the scanner to a PACS (picture archiving and communication systems) image storage device, which provides for economical storage, rapid retrieval of images, access to images acquired with multiple modalities, simultaneous access at multiple sites, and image display. The universal format for PACS image storage and transfer is DICOM (Digital Imaging and Communications in Medicine). Non-image data, such as scanned documents, may be incorporated using consumer industry standard formats like PDF (Portable Document Format), once encapsulated in DICOM.

DICOM can also be used to obtain details of patients and scheduled examinations electronically through the modality worklist service. Another DICOM service, MPPS (Modality Performed Procedure Step), allows the imaging system to send a report about a performed examination including data about the images acquired. Such information may provide a radiology department with a general overall picture of imaging system usage. Unfortunately, the type of information that can be transmitted through such DICOM services is somewhat limited. Thus, there is an unresolved need for other approaches for conveying information from an imaging system.

Aspects of the present application address the above-referenced matters and others.

According to one aspect, a method for exposing imaging system events in connection with an event driven imaging system includes detecting an imaging system event occurred, wherein the imaging system event corresponds to an imaging examination being performed, generating a signal indicative of the detected imaging system event, and transmitting the signal over a computer network for reception by at least one device communicating over the network.

According to another aspect, a method for exposing imaging system protocol information in connection with an imaging system includes detecting at least one of utilizing of, medication to, an addition of, or a deletion of an imaging system protocol from the imaging system, generating a signal indicative of the protocol, and transmitting the signal over a computer network for reception by at least one device communicating over the network.

According to another aspect, an imaging system includes a scanner and a console configured to control the scanner. The console includes a communications interface configured to communicate with at least one device remote from the system via a computer network. The console generates and transmits, via the communications interface and over the computer network, a signal indicative of at least one of an imaging workflow event or an imaging protocol of the imaging system.

The invention may take form in various components and arrangements of components, and in various steps and arrangements of steps. The drawings are only for purposes of illustrating the preferred embodiments and are not to be construed as limiting the invention.

FIG. 1 illustrates an imaging system 100 such as a computed tomography (CT) scanner.

Figure 1:
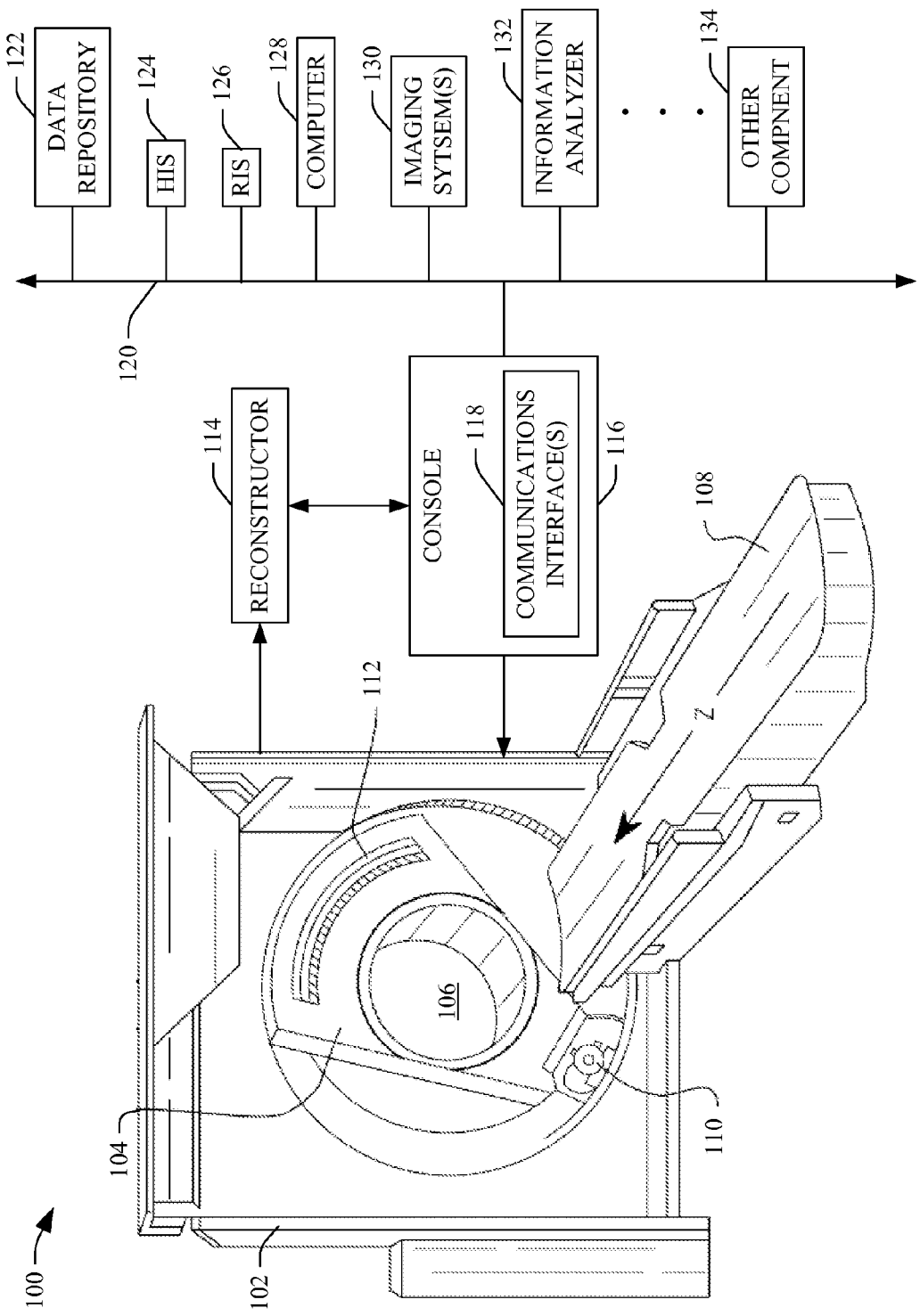
FIG. 1 illustrates an example imaging system.

Other suitable imaging modalities include positron emission tomography (PET), single photon emission tomography (SPECT), magnetic resonance imaging (MRI), ultrasound (US) imaging, digital radiography, and/or other imaging modalities. However, for sake of brevity and explanatory purposes, the following is discussed in connection with a CT scanner.

The imaging system 100 includes a stationary gantry 102 and a rotating gantry 104, which is rotatably supported by the stationary gantry 102. The rotating gantry 104 rotates around an examination region 106 about a longitudinal or z-axis.

A patient support 108, such as a couch, supports a patient in the examination region 106 and is movable along the z-axis in coordination with the rotation of the rotating gantry 104 to facilitate helical, axial, or other desired scanning trajectories.

A radiation source 110, such as an x-ray tube, is supported by and rotates with the rotating gantry 104 around the examination region 106. The radiation source 110 emits generally fan, wedge, or cone shaped radiation that traverses the examination region 106.

A radiation sensitive detector array 112 detects photons emitted by the radiation source 110 that traverse the examination region 106 and generates projection data indicative of the detected radiation.

A reconstructor 114 reconstructs the projection data and generates volumetric image data indicative of the examination region 106. An image processing system can generate one or more images based on the reconstructed image data. Such images can be sent to a filmer, a viewing system, and/or other device.

A general purpose computing system serves as an operator console 116. Software resident on the console 116 allows the operator to control the operation of the system 100, for example, by allowing the operator to initiate scanning, enable automatic or user initiated transfer of imaging events and/or protocols, etc. In one instance, the software includes event (e.g., sensed output, mouse click, key press, program message, etc.) based or driven control software, in which a pre-determined list of imaging related events are detected and handled in a pre-determined manner.

One or more communications interface(s) 118 are configured to allow the console 116 to communicate with at least one component remote from the system 100. Such communication includes, but is not limited to, transmitting (via cable or wirelessly) one or more signals indicative of and thus exposing at least one imaging events, at least one imaging protocol, and/or other information over a computer network 120 (e.g., an intranet, an internet, etc.), the like.

An example of a suitable communications protocol includes, but is not limited to, a Hypertext Transfer Protocol (HTTP) POST request. (Of course, other communication protocols are also contemplated herein.) With a HTTP POST request, the body of the request may include an imaging system event and/or protocol (or change thereto), and optionally a date, time and/or other unique identifier, an event and/or protocol name, scanner information (manufacturer, model, etc.), scanner location, etc.

The request may be issued in real-time as the events occur or the protocol is accessed, or based on a predetermined delay. By way of example, in one instance the delay is configurable and set to at least 15-30 minutes from the actual event or protocol access. Such a delay may facilitate reducing or minimizing the burden on the scanner. In another example, the information is stored locally on the scanner and transferred at a predetermine time(s), such as once day, etc., or automatically, or on demand, or otherwise.

As shown, suitable remote components include, but are not limited to, at least one data repository 122, at least one hospital information system (HIS) 124, at least one radiology information system (RIS) 126, at least one computer 128, at least one other imaging systems 130, at least one information analyzing system 132, and/or at least one other remotely located component 134.

In one instance, the at least one console events includes, but is not limited to, one or more scanner workflow events, such as an event indicative of a user beginning a study, identifying an initial imaging protocol, changing or setting an imaging protocol parameter and/or selecting an imaging protocol, activating and/or deactivation of an injector injecting an agent, starting scanning (for each scan of the study), stopping scanning (for each scan of the study), ending or concluding of the study. The list can be included in a computer readable file and compared with detected imaging events.

The at least one protocol includes, but is not limited to, the default imaging protocol stored on or made available to the imagine system, a stored or available imaging protocol that has been modified by the operator of the system 100 performing scan, just the modification, a protocol that has been deleted, an initially selected imaging protocol and the imaging protocol that was actually used for a scan, and/or other imaging protocol. The protocol name and/or a short description can be provided with the protocol.

It is to be understood that the above-lists are not exhaustive lists and are not limiting. In other instance, other events and/or protocols can be additionally or alternatively be conveyed over the network 120. Moreover, the conveyed events may include default (e.g., facility set) events and/or customized (e.g., clinician dependent) events. Such events may be identified in a computer readable configuration file utilized by the imaging system 100.

The information conveyed over the network 120 can be variously employed.

By way of non-limiting example, in one instance, the imaging system 100 conveys event information over the network 120, for example, to the data repository 122, the HIS 124, the RIS 126, etc. Authorized personnel at the imaging facility of the system 100 can utilize the RIS 126 and/or HIS 124 to observe and/or access the conveyed events, and such information can be used to provide a dashboard of a present or past state of the system 100. Such information may indicate, for example, that the system 100 is currently in use or is available to be used, and can be used to assign imaging resources for a patient, service, calibration, etc.

Additionally or alternatively, the imaging system 100 conveys protocol information over the network 120, for example, to the data repository 122, the HIS 124, the RIS 126, etc. Likewise, authorized personnel at the imaging facility of the system 100 can utilize the RIS 126 and/or HIS 124 to observe and/or access the conveyed protocols, and such information can be used to indicate the particular protocols available at the imaging facility. Such information may assist a radiologist with identifying an imaging protocol for a patient and/or provide the facility with a list of the scanner protocols.

In another non-limiting example, the information analyzer 132 can analyze the conveyed events and/or protocols, and determine various information such how many studies and/or scans were performed during a predetermine time period, the busiest time of day, how long a system has been off-line (e.g., due to preventive and/or corrective maintenance), which protocols are being used on which system 100, how often a particular default protocol is modified, etc. Such information can be used to facilitate optimizing and/or assigning imaging resources, and/or whether to obtain additional imaging resources.

In another instance, the protocols can be conveyed between the imaging system 100 and the at least one imaging systems 130. This allows for sharing protocols and/or protocol changes between imaging systems.

Figure 2:
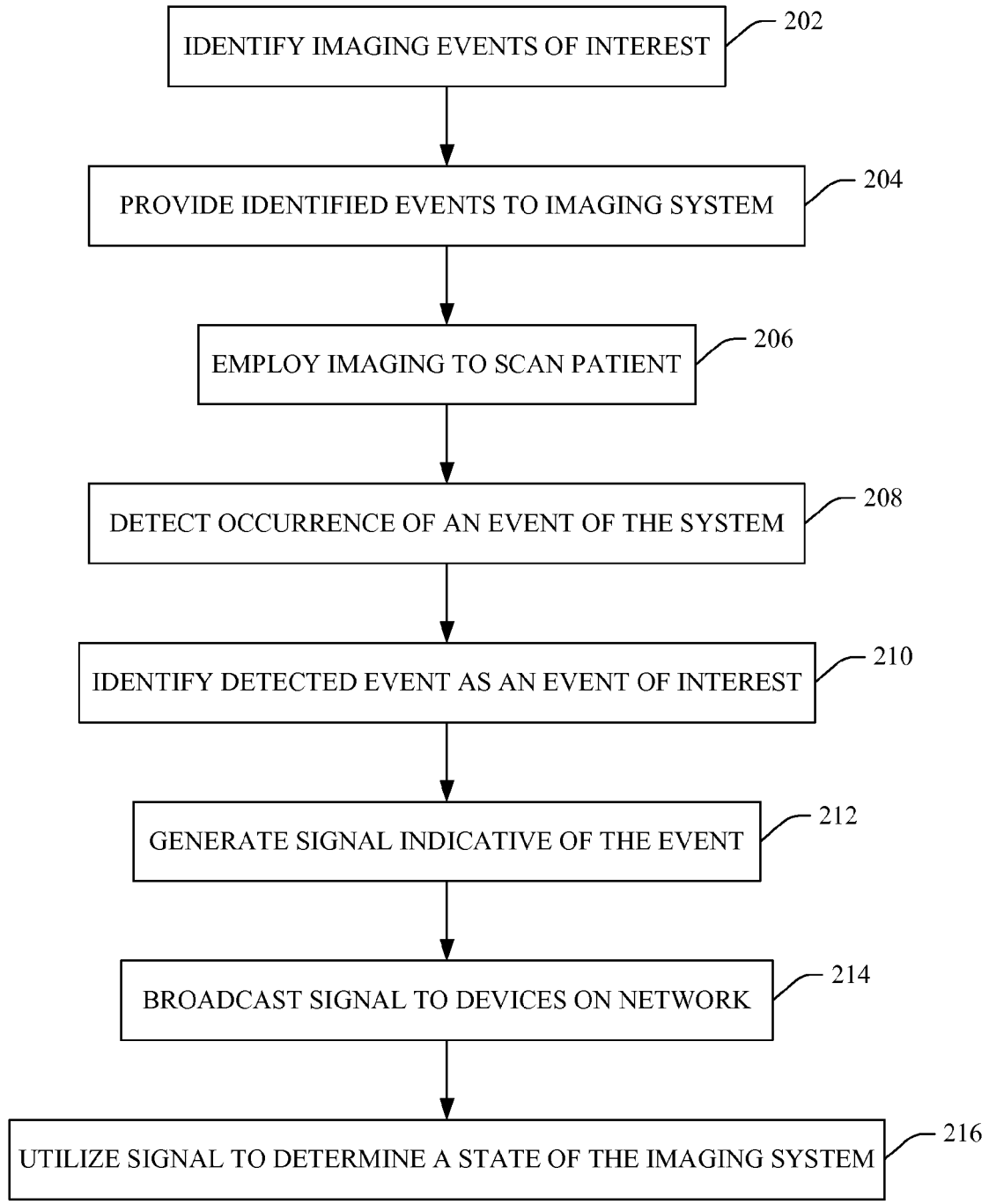
FIG. 2 illustrates an example method for exposing imaging system events.

FIG. 2 illustrates an example method for exposing imaging system events.

It is to be appreciated that the below acts and the ordering thereof is not limiting. As such, other orderings are contemplated herein and one or more acts can be added and/or omitted.

At 202, a set of imaging system events of interest is identified.

At 204, the set of imaging system events of interest are provided in an electronic format to an imaging system.

At 206, the imaging system is employed for performing an examination or study of a patient.

At 208, an occurrence of an event of the imaging system is detected.

At 210, the event is identified as an event in the set of imaging system events of interest.

At 212, a signal including the event and optionally other information about the event is generated.

At 214, the signal is broadcast over a computer network for network device configured to receive the broadcast.

At 216, the signal is utilized to remotely determine a state of the imaging system.

Figure 3:
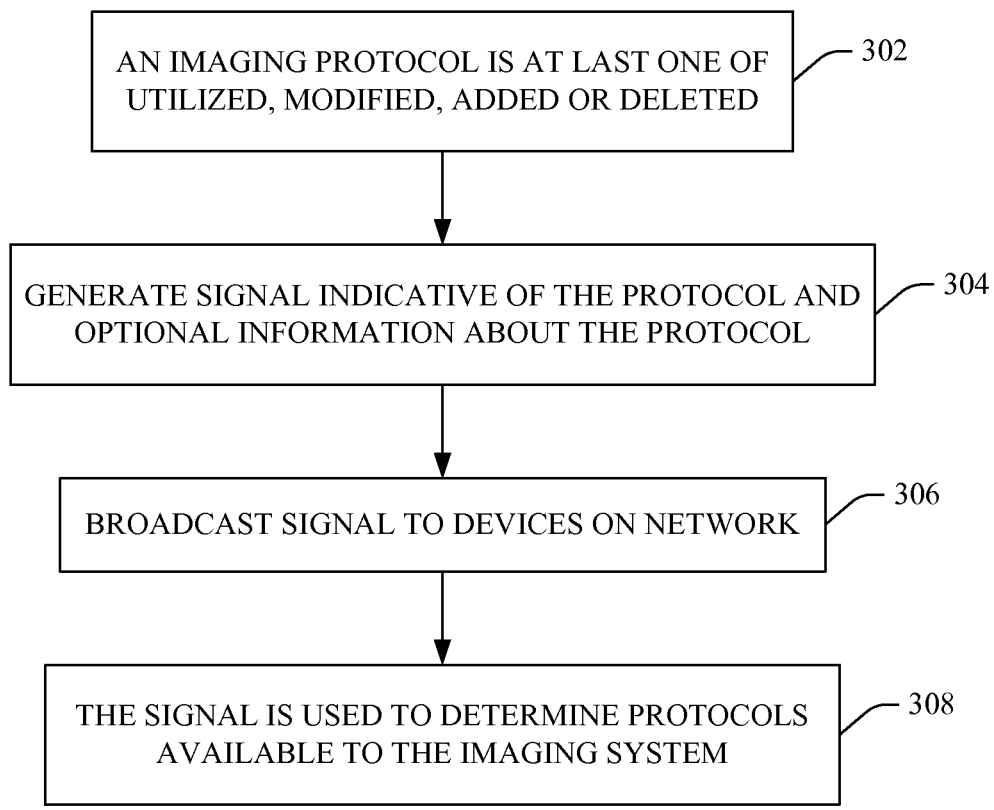
FIG. 3 illustrates an example method for exposing imaging system protocols.

FIG. 3 illustrates an example method for exposing imaging system protocols.

It is to be appreciated that the below acts and the ordering thereof is not limiting. As such, other orderings are contemplated herein and one or more acts can be added and/or omitted.

At 302, an imaging protocol is at least one of utilized, modified, added or deleted from an imaging system.

At 304, a signal including the protocol (or just a change thereto) and optionally other information about the protocol is generated.

At 306, the signal is broadcast over a computer network for network device configured to receive the broadcast.

At 308, the signal is utilized to determine protocols available to the imaging system.

The methods of FIGS. 2 and 3 can be combined for exposing events and protocols and/or other information.

The above may be implemented by way of computer readable instructions, which when executed by a computer processor(s), cause the processor(s) to carry out the described acts. In such a case, the instructions are stored in a computer readable storage medium associated with or otherwise accessible to the relevant computer.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A method for exposing imaging system events in connection with an event driven imaging system, comprising:
    detecting an imaging system event occurred, wherein the imaging system event corresponds to an imaging examination being performed;
    generating a signal indicative of the detected imaging system event; and
    transmitting the signal over a computer network for reception by at least one non-controlling device communicating over the network.

2. The method of claim 1, wherein the event corresponds to at least one of a start of the imaging examination, a selection of an imaging protocol for a scan of the imaging examination, activation of an injector, deactivation of the injector, a start of the scan, an end of the scan, or an end of the imaging examination.

3. The method of claim 1, further comprising:
    generating an electronic file including a list of imaging system events of interest;
    providing access to the file to the imaging system; and
    utilizing the file to detect imaging system events, wherein the list includes the detected imaging system event.

4. The method of claim 1, further comprising:
    transmitting the signal via an HTTP POST request.

5. The method of claim 1, further comprising:
    utilizing the signal to determine a state of the imaging system.

6. The method of claim 1, further comprising:
    utilizing the signal to assign the imaging system for performing an examination.

7. The method of claim 1, further comprising:
    determining event statistics for the imaging system based on the signal.

8. The method of claim 1, further comprising:
    transmitting the signal in real-time.

9. The method of claim 1, further comprising:
    transmitting the signal after a pre-determined delay from the occurrence of the event.

10. The method of claim 1, further comprising:
    transmitting the signal on-demand.

11. The method of claim 1, wherein the signal is received by at least one of a hospital information system or radiology information system.

12. The method of claim 1, further comprising:
    detecting at least one of utilizing, modifying, an adding, or a deleting an imaging system protocol from the imaging system;
    generating a second signal indicative of the protocol; and
    transmitting the second signal over the computer network for reception by the at least one non-controlling device communicating over the network.

13. The method of claim 12, wherein the signal and the second signal are the same signal and concurrently includes event and protocol information.

14. A method for exposing imaging system protocol information in connection with an imaging system, comprising:
    detecting at least one of utilizing, modifying, an adding, or a deleting an imaging system protocol from the imaging system;
    generating a signal indicative of the protocol by a console; and
    transmitting the signal over a computer network for reception by at least one non-console device communicating over the network.

15. The method of claim 14, wherein the signal includes an electronic copy of the protocol.

16. The method of claim 14, wherein the signal includes an electronic copy only of a change to the protocol.

17. The method of claim 14, further comprising:
    transmitting the signal via an HTTP POST request.

18. The method of claim 14, further comprising:
    utilizing the signal to determine protocols available to the imaging system.

19. The method of claim 14, further comprising:
    selecting an imaging protocol for a patient based on the signal.

20. The method of claim 14, wherein the signal is received by at least one of a hospital information system or radiology information system.

21. The method of claim 14, further comprising:
    detecting an imaging system event occurred, wherein the imaging system event corresponds to an imaging examination being performed;
    generating a second signal indicative of the detected imaging system event; and
    transmitting the second signal over the computer network for reception by the at least one device communicating over the network.

22. The method of claim 21, wherein the signal and the second signal are the same signal and concurrently includes event and protocol information.

23. An imaging system, comprising:
    a scanner;
    a console configured to control the scanner, the console, including:

a communications interface configured to communicate with at least one device remote from the system via a computer network, wherein the console generates and transmits, via the communications interface and over the computer network, a signal indicative of at least one of an imaging workflow event or an imaging protocol of the imaging system.

* * * * *